US00PP16070P2

(12) United States Plant Patent
Gilford et al.

(10) Patent No.: US PP16,070 P2
(45) Date of Patent: Oct. 25, 2005

(54) STRAWBERRY PLANT NAMED 'DRISCOLL MALIBU'

(50) Latin Name: *Fragaria×ananassa*
Varietal Denomination: Driscoll Malibu

(75) Inventors: Kristie L. Gilford, Dover, FL (US); Bruce D. Mowrey, Watsonville, CA (US); JoAnne Coss, Salinas, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 123 days.

(21) Appl. No.: 10/679,037

(22) Filed: Oct. 2, 2003

(51) Int. Cl.[7] ..... A01H 5/00
(52) U.S. Cl. ..... Plt./209
(58) Field of Search ..... Plt./209

*Primary Examiner*—Anne Marie Grunberg
*Assistant Examiner*—Annette H Para
(74) *Attorney, Agent, or Firm*—Jones Day

(57) ABSTRACT

This invention relates to a new and distinct variety of strawberry named 'Driscoll Malibu.' The variety is similar to the varieties 'Biscayne', and 'Madeira'. The variety is distinguished from 'Biscayne', and 'Madeira', in particular, by a flat terminal leaflet margin profile, dense petiole pubescence, 20% of plants with single bracts, a very narrow band without achenes on the fruit, and a small hollow fruit center.

5 Drawing Sheets

Latin name of the genus and species of the plant claimed: The variety is botanically identified as *Fragaria×ananassa.*

1. BACKGROUND OF THE INVENTION

The new variety originated as a result of a controlled cross between the strawberry plants 'Marathon' (U.S. Plant Pat. No. 12,817) and 'Sonora' (U.S. Plant Pat. No. 13,386) in an ongoing breeding program, and was discovered as a seedling in Hillsborough Country, Fla. in 1998. The original seedling of the new cultivar was asexually propagated by stolons in a Shasta County, Calif. Propagules were transplanted to a controlled breeding plot in Hillsborough County, Fla., where the variety was identified and selected for further evaluation. 'Driscoll Malibu' was subsequently asexually propagated and underwent further testing in Hillsborough Country, Fla. for three years. This propagation and testing has demonstrated that the combination of traits disclosed herein which characterize the new variety are fixed and retained true to type through successive generations of asexual reproduction.

2. SUMMARY OF THE INVENTION

The present invention relates to a new and distinct variety of strawberry named 'Driscoll Malibu'. The new variety is distinguished from other varieties by a number of characteristics as set forth in Tables 1–4.

3. COMPARISON TO SIMILAR VARIETIES

The varieties which we believe to be similar to 'Driscoll Malibu' from those known to us are 'Biscayne' (U.S. Plant Pat. No. 12,186) and 'Madeira' (U.S. Plant Pat. No. 14,109). There are several characteristics of the new variety that are different from, or not possessed by 'Biscayne' and 'Madeira'. The new variety is distinguished from 'Biscayne' and 'Madeira' by having, for example, a flat terminal leaflet margin profile, dense petiole pubescence, 20% of plants with single bracts, a very narrow band without achenes on the fruit, and a small hollow fruit center.

4. BRIEF DESCRIPTION OF THE DRAWINGS

The accompanying photographs show typical specimens of the new variety, including fruit, foliage, and flowers, in color as nearly true as it is reasonably possible to make in color illustrations of these characteristics.

5. DESCRIPTION OF THE NEW VARIETY

Figure 1:
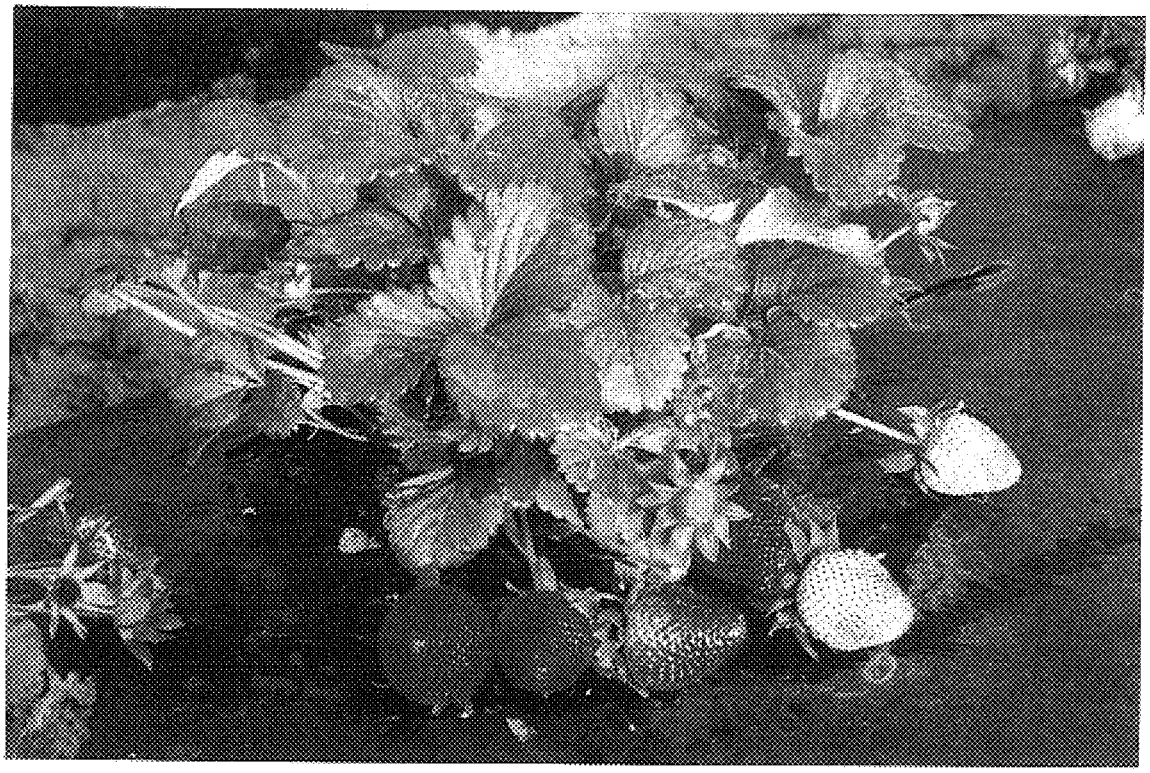
FIG. 1 shows the whole the plant.
Figure 2:
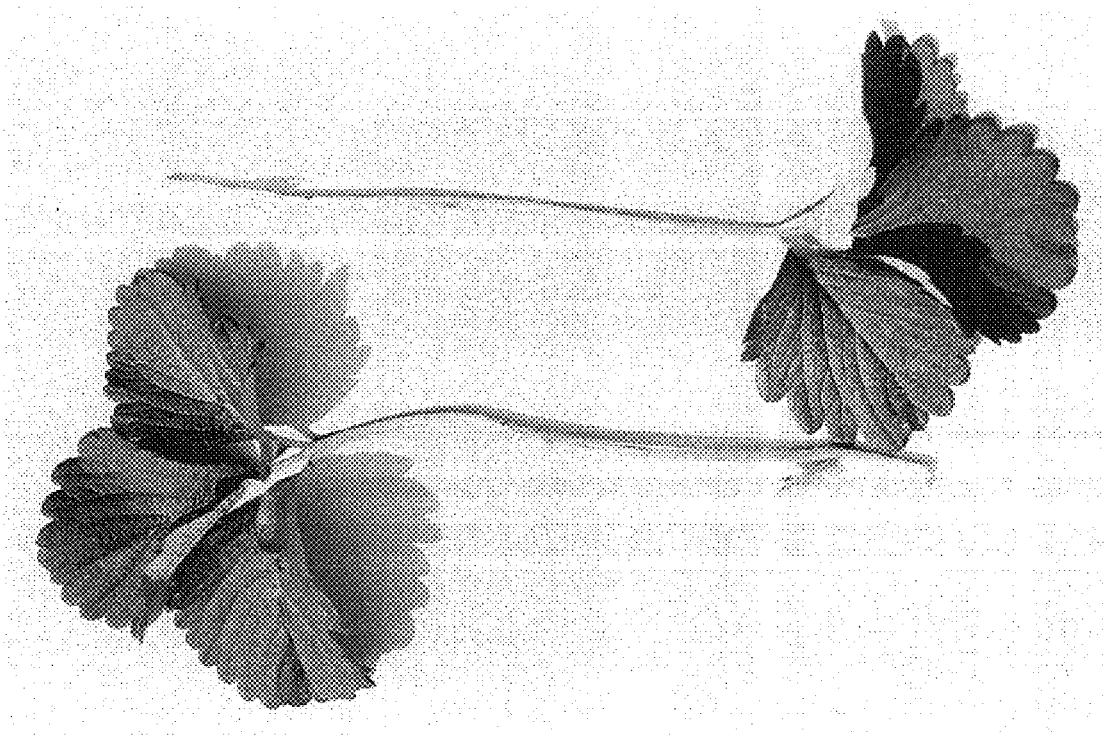
FIG. 2 shows the upper side of the leaves of the plant.
Figure 3:
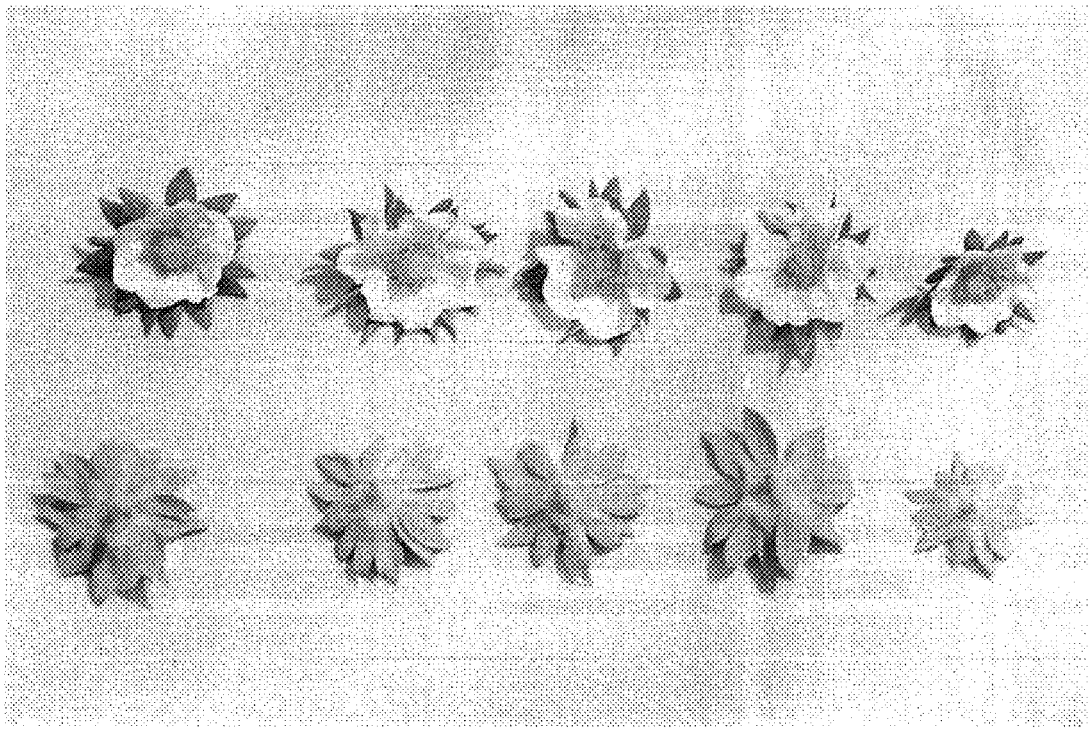
FIG. 3 shows the under side and upperside of the flowers.
Figure 4:
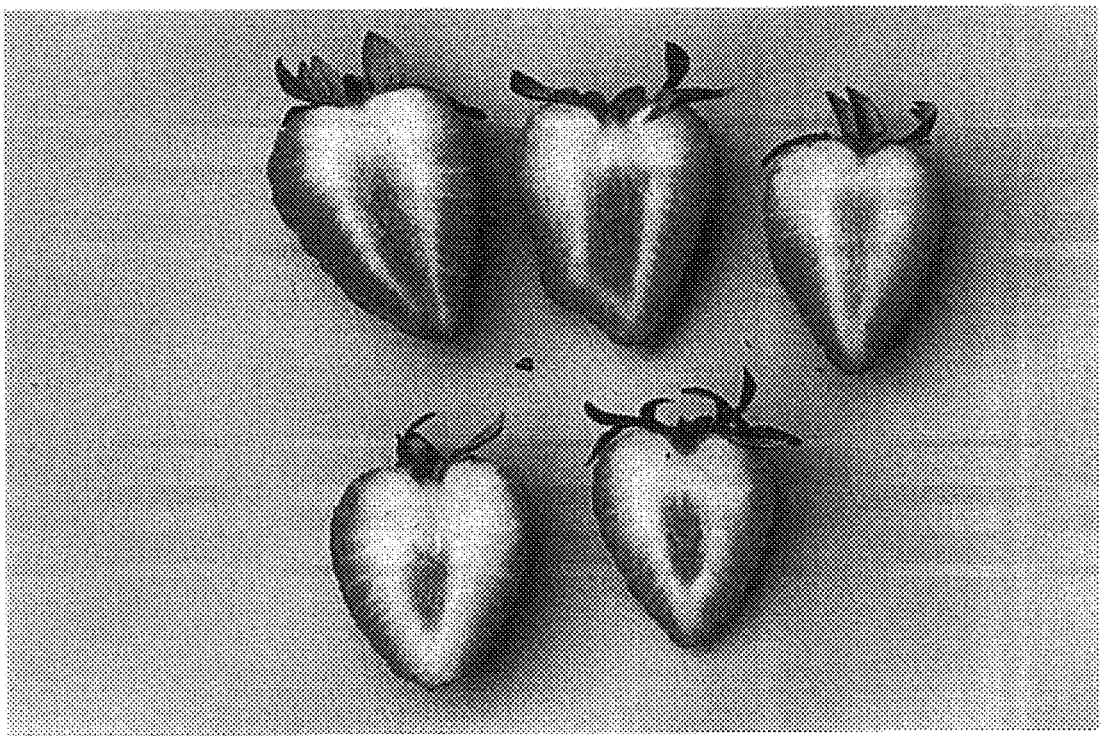
FIG. 4 shows the fruit in longitudinal cross-section.
Figure 5:
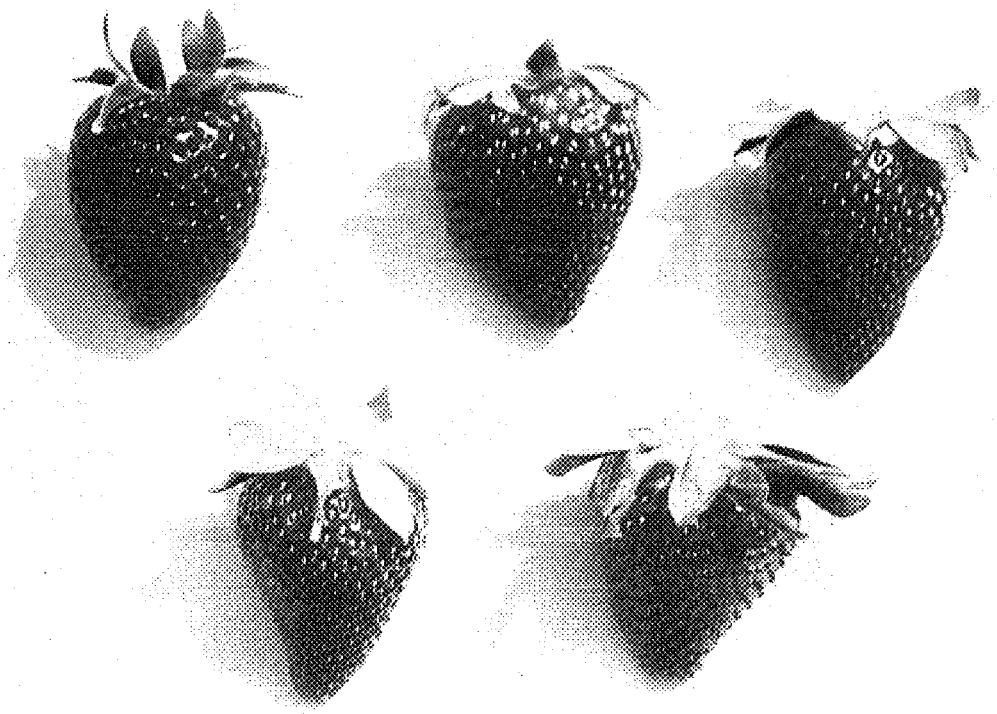
FIG. 5 shows a close-up of the fruit.

The following detailed description of the new variety is based upon observations taken of plants and fruit grown in Hillsborough Country, Fla., U.S.A. This description is in accordance with UPOV terminology. Observations of 'Driscoll Malibu', 'Biscayne', and 'Madeira' were taken in side-by-side comparison in 2002–2003. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

5.2 PROPAGATION

The new variety is principally propagated by way of stolons. Although propagation by stolons is presently preferred, other known methods of propagating strawberry plants may be employed.

5.3. CHARACTERISTICS OF THE NEW VARIETY

Information on the new variety is presented in Tables 1, 2, 3 and 4. In the tables, the flowers described are secondary flowers except where indicated. The fruit described is the secondary fruit on one-year-old plants. Fruit and flower measurements are an average of both primary and secondary fruit and flowers. Flowers of 'Driscoll Malibu' are fully self-fertile and typical of the species. The average size of the hollow fruit center of 'Driscoll Malibu' is 8.0 mm. 'Driscoll Malibu' differs from its maternal parent 'Marathon' by possessing darker red fruit and having superior shelf-life. Plants of 'Driscoll Malibu' are less vigorous and more compact than those of 'Marathon.' 'Driscoll Malibu' differs from its paternal parent 'Sonora' by being partially everbearing, while 'Sonora' is fully everbearing. In addition, the fruit of 'Driscoll Malibu' is brighter red than those of 'Sonora.'

Table 1 provides information on the plant and fruit characteristics of the new variety 'Driscoll Malibu' compared with characteristics of 'Biscayne' and 'Madeira'. Table 2 provides additional information of the plant and fruit characteristics of the new variety 'Driscoll Malibu' compared with characteristics of the varieties 'Biscayne' and 'Madeira'. Table 3 provides reactions of the new variety to pests and diseases compared with reactions of the varieties 'Biscayne' and 'Madeira'. Table 4 provides isozyme characteristics of the new variety as compared to that of the varieties 'Biscayne' and 'Madeira'.

TABLE 1

QUANTITATIVE COMPARISON OF 'DRISCOLL MALIBU', 'BISCAYNE', AND 'MADEIRA'

| | 'DRISCOLL MALIBU' | 'BISCAYNE' | 'MADEIRA' |
|---|---|---|---|
| Plant Characteristics | | | |
| Height of Plant (cm) | 13.6 | 13.5 | 15.8 |
| Spread of Plant (cm) | 34.1 | 32.6 | 36.1 |
| Number of Crowns | 3.9 | 5.2 | 4.2 |
| Leaf Characteristics | | | |
| Terminal Leaflet Length (cm) | 8.7 | 8.6 | 9.4 |
| Terminal Leaflet Width (cm) | 8.8 | 8.8 | 8.4 |
| Terminal Leaflet Length/Width Ratio | 0.99 | 0.98 | 1.12 |
| # Teeth/Terminal Leaflet | 20.1 | 23.8 | 18.8 |
| Color of upper side | 141A light to medium green | 137A light green | 147A dark green |
| Color of under side | 139C light gray green | 139C light gray green | 137B light gray green |
| Petiole Length (cm) | 11.4 | 11.7 | 11.0 |
| Petiole Color | 144B yellow-green | 141D yellow-green | 144B yellow-green |
| Bract Frequency | 20% typically single | 60% typically double | 80% typically double |
| Stipule Length (cm) | 3.8 | 3.5 | 3.2 |
| Stipule Width (cm) | 2.0 | 1.9 | 2.2 |
| Stolon Characteristics | | | |
| Anthocyanin color | 58A red purple | 59B red purple | 59C red purple |
| Diameter at bract (mm) | 3.35 | 3.29 | 2.77 |
| Avg. # of Daughter plants/Mother (2002 Nursery) | 46 | 59 | 59 |
| Flower Characteristics | | | |
| Petal Length (cm) | 1.3 | 1.4 | 1.4 |
| Petal Width (cm) | 1.4 | 1.6 | 1.5 |
| Petal Length/Width Ratio | 0.94 | 0.85 | 0.91 |
| Flower Diameter (cm) | 3.2 | 3.5 | 3.3 |
| Calyx Diameter (cm) | 4.1 | 4.6 | 4.1 |

TABLE 1-continued

QUANTITATIVE COMPARISON OF 'DRISCOLL MALIBU', 'BISCAYNE', AND 'MADEIRA'

| | 'DRISCOLL MALIBU' | 'BISCAYNE' | 'MADEIRA' |
|---|---|---|---|
| Petal Color | 155C white | 155C white | 155C white |
| Fruiting Truss Length (cm) | 13.3 | 12.5 | 12.0 |
| Fruit Characteristics | | | |
| Fruit Length (cm) | 4.8 | 4.9 | 5.0 |
| Fruit Width (cm) | 3.8 | 4.1 | 4.3 |
| Fruit Length/Width Ratio | 1.28 | 1.20 | 1.18 |
| Average Berry Weight (g) | 23.4 | 24.7 | 24.3 |
| External Color | 46B red | 46B red | 46A dark red |
| Internal Color | 48C orange red | 44A medium red | 43A medium red |
| 2002–2003 Yield (g/plant) | 199 | 143 | 247 |

TABLE 2

QUALITATIVE COMPARISON OF 'DRISCOLL MALIBU', 'BISCAYNE', AND 'MADEIRA'

| | 'DRISCOLL MALIBU' | 'BISCAYNE' | 'MADEIRA' |
|---|---|---|---|
| Plant | | | |
| Habit | globose | flat globose | flat globose |
| Density | medium | medium | medium |
| Vigor | weak to medium | strong | strong |
| Leaf | | | |
| Shape in cross section | slightly concave to flat | concave | concave |
| Interveinal blistering | medium | weak | medium |
| Glossiness | weak | medium | medium |
| Number of leaflets | three only | three only | three only |
| Terminal leaflet margin profile | flat | revolute | revolute |
| Terminal leaflet shape of base | rounded | rounded | obtuse |
| Terminal leaflet shape of teeth | obtuse to rounded | rounded | rounded |
| Stipule pubescence | medium | medium | medium |
| Petiole pubescence | dense | medium | medium |
| Petiole pose of hairs | downwards | outwards | downwards |
| Stolon | | | |
| Amount | medium | many | many |
| Anthocyanin coloration | medium to strong | strong | strong to very strong |
| Thickness | medium to thick | medium | medium to thick |
| Pubescence | medium | medium | medium |
| Inflorescence | | | |
| Position relative to foliage | level to above | level | beneath |
| Diameter of calyx relative to corolla on secondary flowers | larger | larger | larger |
| Diameter of inner calyx relative to outer on secondary flowers | larger | same size | same size |
| Spacing of petals | overlapping | overlapping | overlapping |

TABLE 2-continued

QUALITATIVE COMPARISON OF 'DRISCOLL MALIBU', 'BISCAYNE', AND 'MADEIRA'

| | 'DRISCOLL MALIBU' | 'BISCAYNE' | 'MADEIRA' |
|---|---|---|---|
| Fruiting Truss | | | |
| Attitude at first picking | prostrate | prostrate | prostrate |
| Fruit | | | |
| Predominant shape | conical | conical | conical |
| Difference in shapes between primary and secondary fruits | slight | slight | slight |
| Band without achenes | very narrow | narrow | narrow |
| Unevenness of surface | medium | weak | weak |
| Evenness of color uneven | slightly uneven | even | even |
| Glossiness | strong | strong | strong |
| Insertion of achenes | below to level with the surface | level with surface | level with surface |
| Insertion of calyx | level | level | level |
| Pose of the calyx segments | reflexed | spreading | reflexed |
| Size of calyx in relation to fruit on secondary fruit | same size to larger | larger | smaller |
| Adherence of calyx | strong | strong | strong |
| Firmness of flesh | soft to medium | firm | medium |
| Evenness of flesh color | slightly uneven | slightly uneven | slightly uneven |
| Distribution of flesh color | marginal and central | marginal and central | marginal and central |
| Hollow center size | small | large | medium |
| Sweetness | medium | strong | weak to medium |
| Texture when tasted | medium | fine | fine |
| Acidity | medium | medium | weak to medium |
| Time of Flowering | very early | early | very early |
| Harvest Interval in 2002–2003 | late November through late March | early December through late March | late November through late March |
| Type of Bearing | partially evebearing | partially everbearing | partially everbearing |

5.4. REACTION TO STRESS, PESTS, AND DISEASE

TABLE 3

REACTIONS TO PESTS AND DISEASES FOR 'DRISCOLL MALIBU', 'BISCAYNE', AND 'MADEIRA'

| | 'DRISCOLL MALIBU' | 'BISCAYNE' | 'MADEIRA' |
|---|---|---|---|
| Reaction to Pests | | | |
| *Tetranychus urticae* | susceptible | susceptible | susceptible |
| *Lygus hesperus* | susceptible | susceptible | susceptible |
| Reaction To Diseases | | | |
| Botrytis fruit rot | susceptible | susceptible | susceptible |
| Powdery mildew | moderately susceptible | moderately susceptible | moderately susceptible |
| *Verticillium* wilt | highly susceptible | susceptible | moderately susceptible |
| Strawberry Mottle Virus | susceptible | susceptible | partially resistant |
| *Xanthomonas fragariae* | moderately susceptible | moderately susceptible | moderately susceptible |

5.5. ISOZYME ANALYSIS

In addition to the morphological description above, the new cultivar 'Driscoll Malibu' has been analyzed to obtain an indication of its genetic makeup to provide further means for identifying the new variety and distinguishing it from other somewhat similar and/or related strawberry varieties. Specifically, leaf samples of 'Driscoll Malibu', 'Biscayne', and 'Madeira' were analyzed by electrophoresis for isozyme patterns of the enzymes phosphoglucoisomerase ("PGI"), leucine aminopeptidase ("LAP") and phosphoglucomutase ("PGM"). See J. Amer. Soc. Hort. Sci. 106:684–687. Isozyme characterization of the three varieties is presented in Table 4, with the letters representing the banding patterns for each enzyme as designated in the above-identified article.

TABLE 4

ISOZYME ANALYSIS FOR 'DRISCOLL MALIBU', 'BISCAYNE', AND 'MADEIRA'

| Locus | 'DRISCOLL MALIBU' | 'BISCAYNE' | 'MADEIRA' |
|---|---|---|---|
| PGI | A1 | A1 | A1 |
| LAP | B3 | B3 | B1 |
| PGM | C4 | C4 | C2 |

What is claimed:

1. A new and distinct variety of strawberry plant, substantially as shown and described.

* * * * *